(12) United States Patent
O'Lenick, Jr. et al.

(10) Patent No.: US 6,982,078 B1
(45) Date of Patent: Jan. 3, 2006

(54) DIMER AMIDOPROPYL DIMETHYL POLY-QUATERNARY COMPOUNDS

(75) Inventors: Anthony J. O'Lenick, Jr., Dacula, GA (US); Thomas G. O'Lenick, Dacula, GA (US)

(73) Assignee: SurfaTech Corporation, Dacula, GA (US)

( * ) Notice: Subject to any disclaimer, the term of this patent is extended or adjusted under 35 U.S.C. 154(b) by 96 days.

(21) Appl. No.: 10/807,585

(22) Filed: Mar. 24, 2004

(51) Int. Cl.
*A61K 7/075* (2006.01)

(52) U.S. Cl. .................... 424/70.28; 424/70.1; 554/52; 554/51; 514/613; 514/616; 514/642

(58) Field of Classification Search ............... 424/70.1, 424/70.28; 514/613, 616, 642; 554/51, 554/52
See application file for complete search history.

(56) References Cited

U.S. PATENT DOCUMENTS 6,331,293 B1   12/2001  Smith et al.

*Primary Examiner*—Deborah D. Carr

(57) ABSTRACT

The present invention relates to a novel class of polymeric compounds having specific quaternized amine based upon a dimer acid amido amine quaternary compound. Dimer acid is a C-36 diacid having a cyclic structure and two amine groups that allow for the synthesis of a high molecular weight cationic compound which is extremely substantitive to human skin and are well tolerated by human tissue making them suitable for use preparation of barrier products for personal care applications.

20 Claims, No Drawings

DIMER AMIDOPROPYL DIMETHYL POLY-QUATERNARY COMPOUNDS

FIELD OF THE INVENTION

The present invention relates to a novel class of polymeric compounds having specific quaternized amine based upon a dimer acid amido amine quaternary compound. Dimer acid is a C-36 diacid having a cyclic structure and two amine groups that allow for the synthesis of a high molecular weight cationic compound which is extremely substantitive to human skin and are well tolerated by human tissue making them suitable for use preparation of barrier products for personal care applications.

BACKGROUND OF THE INVENTION

It is very desirable to provide a material from aqueous solution that will condition the hair and still be compatible with anionic surfactants. This allows for the preparation of clear two in one shampoo systems, clear 2 in one shower gels, and clear two in one bath products. By two in one products in meant, a product that contains both anionic surfactant, most commonly sulfates and ether sulfates and a cationic conditioning agent. The anionic surfactant is the detergent, which cleans the hair or skin, and the cationic product is for conditioning providing softness, slip and feels to the skin. The problem with such product has always been the incompatibility of the anionic and cationic surfactants with each other. When many of these products are present in the same solution an insoluble salt forms making a cosmetically unacceptable white gunk that does not stay in solution.

As will become clear, by making a very large molecule the present invention results in a we call a soft quaternary compound. By soft quaternary compound is meant one that not withstanding its cationic charge is of a structure so that when placed in water along with the anionic surfactant, a clear stable solution is obtained. Surprisingly, because of the high molecular weight of the quaternary compound, the deposition on the hair and skin is increased. While not wanting to be held to only one mechanism, we believe there rather than a precipitate observed with so-called hard quats, compounds of the present invention form a self-assembling complex between the anionic and cationic surfactant. This complex, while water-soluble is large enough to disrupt hydrogen bonding between water molecules, and as such energetically, the complex will be deposited on the skin or hair leaving the remaining solution at the lowers free energy level.

The self-assembling aspect of the present invention, which we believe is the result of orientation of the salt of the cationic compounds of the present invention and the anionic surfactants present in solution, can be demonstrated by the fact that upon initial mixing of the components, a hazy or cloudy dispersion occurs. With suitable mixing, this hazy dispersion becomes a solution and the viscosity increases.

The compounds of the present invention can be formulated into body washes and other skin products and hair care products to provide a "delivery system" for conditioning the hair or skin. The high molecular weight of the quat and the fact that the point charges are far apart in the molecule results in through and efficient deposition on the hair or skin. This provides uniformity of conditioning agent over the entire hair of skin surface. This is particularly important for applications on hair for people with long hair. In general the long hair is more damaged, dry and in need of conditioning at the tip area, than near the root. The hair closest to the scalp is newer, less damaged, and less in need of conditioning. This dichotomy of hair condition is more effectively treated by the complexes formed by the current invention than by other quats. In addition, the di-nature of the compounds provides for outstanding substantivity of the molecule allow for very mild natural like materials that can be used in products where low irritation is important.

U.S. Pat. No. 6,331,293 issued Dec. 18, 2001 to Smith et al describes phosphobetaines that are derived from dimer acid. Unlike the compounds of the present invention, these materials are amphoteric surfactants and are barriers when applied to the skin. It is stated that the compounds are "extremely substantitive to human skin and are well tolerated by human tissue making them suitable for use preparation of barrier products for personal care applications". Unlike these materials, the compounds of the present invention are not amphoterics, but are quats, are not barriers but are conditioning agents that do not build up on the hair or skin.

SUMMARY OF THE INVENTION

Objective of the Invention

It is the objective of the invention to provide a novel series of polymeric dimer amido quaternary compounds and a process of its use which comprises contacting the skin with an effective conditioning concentration of the novel quaternary compounds when applied in aqueous solution containing anionic surfactants. These anionic surfactants are preferably fatty sulfates and fatty ether sulfates having between 1 and 4 moles of ethylene oxide present. The polymeric nature of these materials makes them very substantive and minimally penetrating to the skin, making them both non-toxic and non-irritating.

In accordance with the present invention, we have now been discovered novel quaternary compound, which conforms to the following structure:

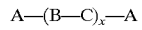

wherein:

A is

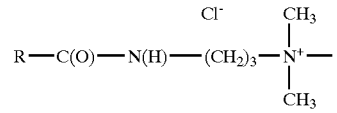

wherein;

R is alkyl having between 7 and 27 carbon atoms, and includes linear, branched, saturated, unsaturated and poly-unsaturated;

B is —CH$_2$CH(OH)CH$_2$—

C is selected from the group consisting of

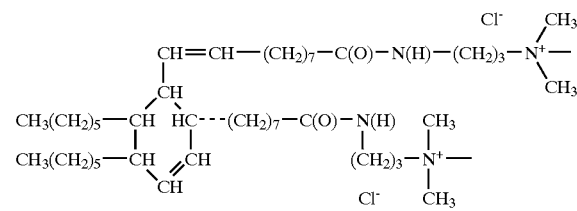

and

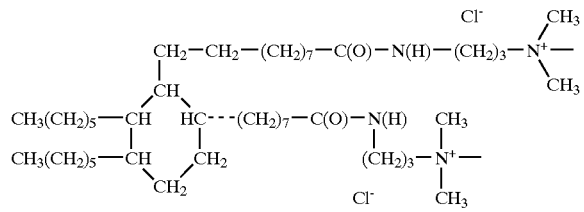

wherein;
x is an integer ranging from 1 to 2000.

The difference between the two dimer species is that one of them has no double bond in the cyclic structure, while the first has a double bond. The double bond is removed by hydrogenation of the acid prior to making the quaternary compound. This variation has lighter color and better oxidative stability, making it prized for cosmetic applications where a water white product is desired. Consumers consider water white products as cleaner and more appealing over yellow products.

The present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

The process for conditioning hair comprises contacting the hair with an effective conditioning concentration of a quaternary compound, which conforms to the following structure:

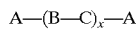

wherein:
A is

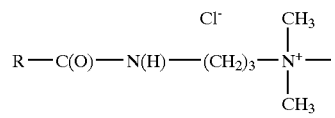

wherein;
R is alkyl having between 7 and 27 carbon atoms, and includes linear, branched, saturated, unsaturated and polyunsaturated;
B is —CH$_2$CH(OH)CH$_2$—
C is selected from the group consisting of:

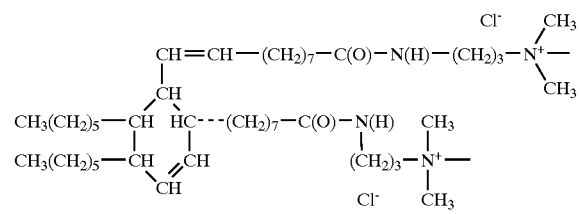

and

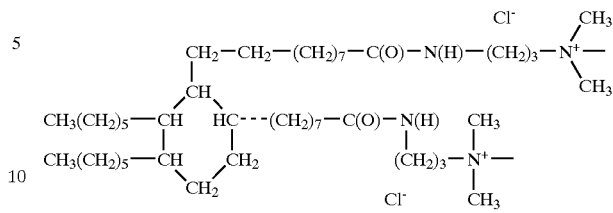

wherein;
x is an integer ranging from 1 to 2000.

The preferred effective conditioning concentration ranges from 0.5% to 25% by weight.

The polymers of the present invention are made in polar solvent, typically water, but can also be made in propylene glycol, polyoxyalkylene glycols and PEG/PPG dimethicone or combinations thereof. The selection of the proper solvent or combinations of solvents will determine the viscosity of the final polymer.

The use of PEG/PPG dimethicone as a solvent results not only in a relatively low viscosity product, but also results in a composition that has extremely efficient deposition on hair and skin, making the compositions highly desirable in personal care applications.

PREFERRED EMBODIMENTS

In a preferred embodiment R is —CH$_3$(CH$_2$)$_6$—.
In a preferred embodiment, R is —CH$_3$(CH$_2$)$_8$—.
In a preferred embodiment, R is —CH$_3$(CH$_2$)$_{10}$—.
In a preferred embodiment R is —CH$_3$(CH$_2$)$_{12}$—.
In a preferred embodiment, R is —CH$_3$(CH$_2$)$_{14}$—.
In a preferred embodiment, R is —CH$_3$(CH$_2$)$_{16}$—.
In a preferred embodiment R is —CH$_3$(CH$_2$)$_{18}$—.
In a preferred embodiment, R is —CH$_3$(CH$_2$)$_{20}$—.
In a preferred embodiment, R is —CH$_3$(CH$_2$)$_{22}$—.
In a preferred embodiment R is —CH$_3$(CH$_2$)$_{24}$—.
In a preferred embodiment, R is —CH$_3$(CH$_2$)$_{26}$—.
In a preferred embodiment x is 1.

DETAILED DESCRIPTION OF THE INVENTION

The present invention is directed to novel cationic compounds, which conform to one of the following structure:

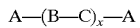

wherein:
A is

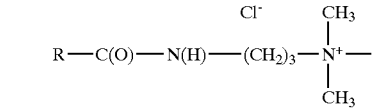

wherein;
R is alkyl having between 7 and 27 carbon atoms, and includes linear, branched, saturated, unsaturated and polyunsaturated;
B is —CH$_2$CH(OH)CH$_2$—

C is selected from the group consisting of

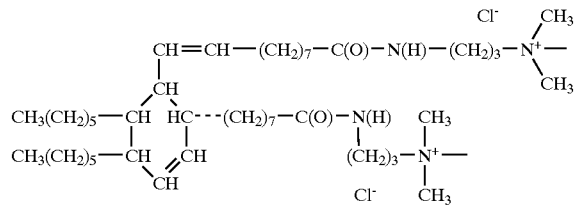

and

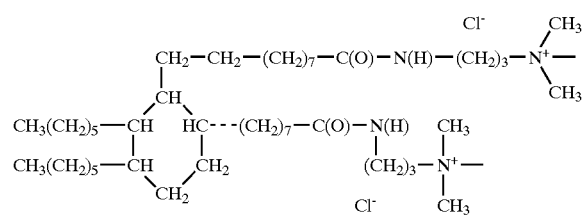

wherein;

x is an integer ranging from 1 to 2000.

The compounds of the present invention are made reaction of the 1,3 dichloro, 2 hydroxy propane with a mixture of mono tertiary amines and di-tertiary amines in a polar solvent.

Monofunctional Tertiary Amines

Monofunctional tertiary amines confirm to the following structure:

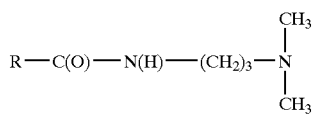

wherein;

R is alkyl having between 7 and 27 carbon atoms, and includes linear, branched, saturated, unsaturated and polyunsaturated, and Di-functional Tertiary Amines Di-functional tertiary amines are selected from the group consisting of compounds conforming to the following structures:

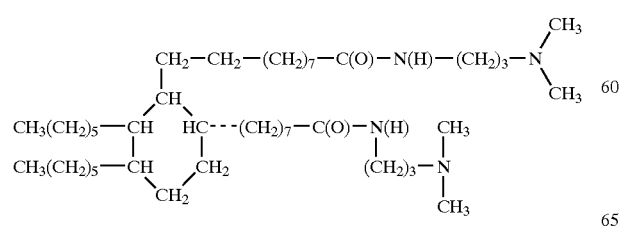

and

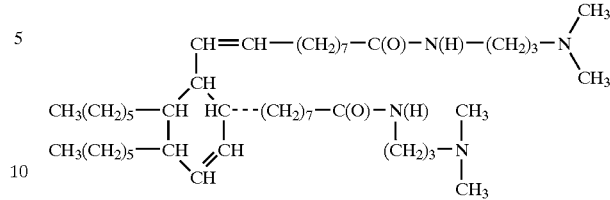

under aqueous conditions.

The polymerization process continues with the monofunctional tertiary amine being the chain terminator (A) unit, the hydroxy-propyl group being the (B) unit and the dysfunctional tertiary amine being the (c) unit. The product of the present invention is thereby attained as a polyquaternium. The higher the concentration of monofunctional tertiary amine, the lower the value of "x". If no di-tertiary amine is added, x is 0, resulting in a bis-quat not a polymer. The polymer is not made with vinyl monomer, thereby making it vinyl monomer free and avoiding the toxicological problems inherent to levels of unreacted monomer left in vinyl polymers.

The compatibility of this novel quaternary compounds of the invention with human tissue, i.e., dermal and eye tissue has been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

EXAMPLES

Dimer Acid and Hydrogenated Dimer Acid

Dimer acid and hydrogenated dimer acids are items of commerce commercially available from several suppliers, one of which is Cognis Corporation, formerly the Emery Division of Henkel.

Dimer acid conforms to the following structure;

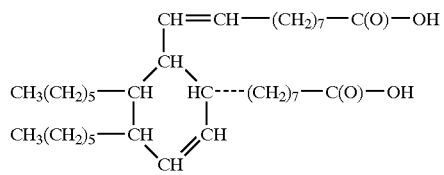

Hydrogenated dimer acid conforms to the following structure;

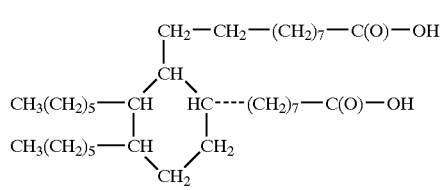

DMAPA

Dimethylaminopropyl Amine is an item of commerce available from a variety of sources including Dow Chemical.

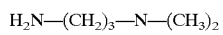

1,3 di-chloro-2-hydroxy-propane 1,3 di-chloro-2-hydroxy-propane is a item of commerce available from a variety of sources including Dixie Chemical. It conforms to the following structure:

Mono-functional Tertiary Amines

Monofunctional Tertiary amines conform to the following structure:

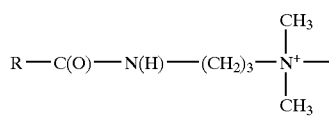

wherein;

R is alkyl having between 7 and 27 carbon atoms, and includes linear, branched, saturated, unsaturated and poly-unsaturated.

They are commercially available from a variety of manufacturers including Siltech LLC, Dacula, Ga.

| Example | R |
|---|---|
| 1 | $C_7H_{13}$ |
| 2 | $C_9H_{17}$ |
| 3 | $C_{11}H_{21}$ |
| 4 | $C_{13}H_{25}$ |
| 5 | $C_{15}H_{29}$ |
| 6 | $C_{17}H_{33}$ |
| 7 | $C_{19}H_{37}$ |
| 8 | $C_{21}H_{41}$ |
| 9 | $C_{23}H_{25}$ |
| 10 | $C_{25}H_{49}$ |
| 11 | $C_{27}H_{51}$ |

Di-functional Tertiary Amines

Example 12

Preparation of Dimer Amido Amine

To 561.0 grams if dimer acid is added 153.0 grams of dimethylaminopropyl amine. The mixture is heated to 180–200° C. and held for 3–8 hours. Once the temperature begins to reach 180° C., water begins to distill off. An excess of dimethylaminopropyl amine is added to speed up the reaction. When the acid value reaches 1.0 mg KOH/gram, the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm. The product is a yellow water insoluble liquid at ambient temperatures.

Example 13

Preparation of Dimer Amido Amine

To 563.0 grams if hydrogenated dimer acid is added 153.0 grams of dimethylaminopropyl amine. The mixture is heated to 180–200° C. and held for 3–8 hours. Once the temperature begins to reach 180° C., water begins to distill off. An excess of dimethylaminopropyl amine is added to speed up the reaction. When the acid value reaches 1.0 mg KOH/gram, the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm.

Example 14–24

Preparation of the Cationic of the Present Invention

Into a suitable reaction flask is charged the specified number of grams of the specified solvent. Next, add the specified number of grams of 1,3 dichloro 2 hydroxy propane. Heat is applied to 90° C. Next, the specified number of grams of the specified dimer amidoamine (either example 12 or 13), followed by the specified number of grams of the specified mono tertiary amine (examples 1–11) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

Example 14–24

| | Solvent | | Mono Amine | | Di Amine | | 1,3 dichloro-2 hydroxy |
|---|---|---|---|---|---|---|---|
| Example | Type | Grams | Example | Grams | Example | Grams | propane (grams) |
| 14 | Water | 185.7 | 1 | 9.6 | 12 | 75.5 | 14.9 |
| 15 | Water | 150.0 | 2 | 5.6 | 13 | 78.8 | 15.5 |
| 16 | DMC | 50.0 | 3 | 2.6 | 12 | 81.4 | 16.1 |
| | Water | 50.0 | | | | | |
| 17 | PG | 300.0 | 4 | 1.4 | 13 | 82.3 | 16.2 |
| 18 | Water | 81.8 | 5 | 2.3 | 12 | 81.6 | 16.1 |
| 19 | Water | 100.0 | 6 | 25.5 | 12 | 62.3 | 12.3 |
| 20 | PEG | 185.7 | 7 | 6.8 | 13 | 77.8 | 15.3 |

-continued

| | Solvent | | Mono Amine | | Di Amine | | 1,3 dichloro-2 hydroxy |
| Example | Type | Grams | Example | Grams | Example | Grams | propane (grams) |
| --- | --- | --- | --- | --- | --- | --- | --- |
| 21 | Water | 185.7 | 8 | 0.4 | 12 | 83.2 | 16.4 |
| 22 | Water | 150.0 | 9 | 17.3 | 12 | 69.0 | 13.6 |
| 23 | Water | 75.0 | 10 | 4.3 | 12 | 80.0 | 15.8 |
|    | PG    | 75.0 |    |      |    |      |      |
| 24 | Water | 75.0 | 11 | 0.1 | 12 | 83.4 | 16.5 |
|    | PG    | 75.0 |    |      |    |      |      |

DMC is PEG10 Dimethicone a commercial product marketed by Siltech LLC Dacula, Ga. as SILSURF Di1010.
PEG is polyoxyethylene glycol having a molecular weight of 400, marketed commercially by Phoenix Chemical Inc. Somerville, N.J.
PG is propylene glycol, marketed commercially by Phoenix Chemical Inc Somerville, N.J.

Additional Information

| Example | x value | % Solids |
| --- | --- | --- |
| 14 | 10 | 35 |
| 15 | 20 | 40 |
| 16 | 50 | 50 |
| 17 | 10 | 25 |
| 18 | 1 | 55 |
| 19 | 67 | 50 |
| 20 | 5 | 35 |
| 21 | 600 | 35 |
| 22 | 10 | 40 |
| 23 | 50 | 40 |
| 24 | 2000 | 35 |

The products of the present invention range from low viscosity (300 cps for example 20) to a solid gel for example 24. The key to viscosity is the degree of polymerization (d.p.) which is reflected in the "x" value. As the "x" value increases the molecular weight of the resultant polymer increases and the % by weight of the mono tertiary amine decreases. Viscosity can also be lowered by using a non-aqueous polar solvent like propylene glycol or butylene glycol.

Applications Examples

The higher the molecular weight, the less likely the compound is to penetrate the skin. Since contact with skin is expected in washing the hair, even for hair use the higher molecular weight components are desired. The polymers of the present invention are not made by free radical polymerization. Consequently, they have no residual monomer content. This has become a major issue in selecting polymers for personal care.

The compounds of the present invention provide outstanding wet comb and conditioning properties to hair. They reduce static build up and provide gloss. The polymers of the present invention provide an outstanding smooth dry feel on the skin. The polymers of the present invention are non-toxic, and non-irritating.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for conditioning hair, which comprises contacting the hair with an effective conditioning concentration of a quaternary compound, which conforms to the following structure:

$$A—(B—C)_x—A$$

wherein:

A is

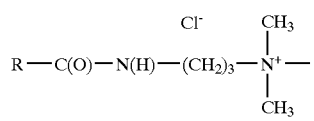

wherein;

R is alkyl having between 7 and 27 carbon atoms, and includes linear, branched, saturated, unsaturated and polyunsaturated;

B is —CH$_2$CH(OH)CH$_2$—

C is selected from the group consisting of:

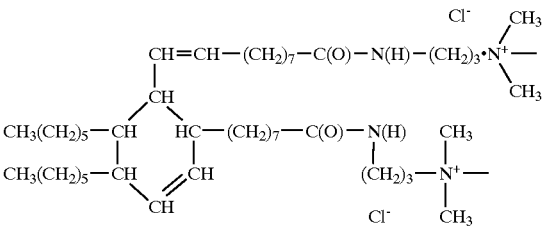

and

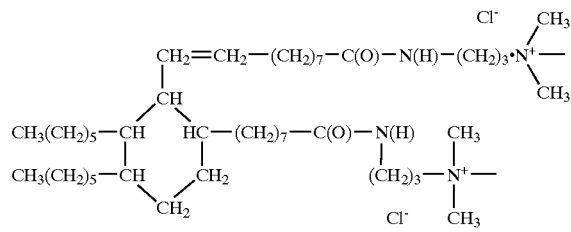

wherein;
x is an integer ranging from 1 to 2000.

2. A process of claim 1 wherein said effective conditioning concentration ranges from 1.0% to 25% by weight.
3. A process of claim 1 wherein R is —$CH_3(CH_2)_{12}$—.
4. A process of claim 1 wherein R is —$CH_3(CH_2)_{14}$—.
5. A process of claim 1 wherein R is —$CH_3(CH_2)_{18}$—.
6. A process of claim 2 wherein R is —$CH_3(CH_2)_{12}$—.
7. A process of claim 2 wherein R is —$CH_3(CH_2)_{14}$—.
8. A process of claim 2 wherein R is —$CH_3(CH_2)_{18}$—.
9. A quaternary compound, which conforms to the following structure:

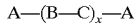

wherein:
A is

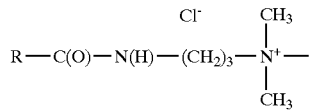

wherein;
R is alkyl having between 7 and 27 carbon atoms, and includes linear, branched, saturated, unsaturated and polyunsaturated;
B is —$CH_2CH(OH)CH_2$—
C is selected from the group consisting of

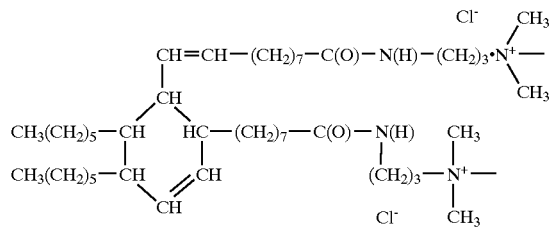

and

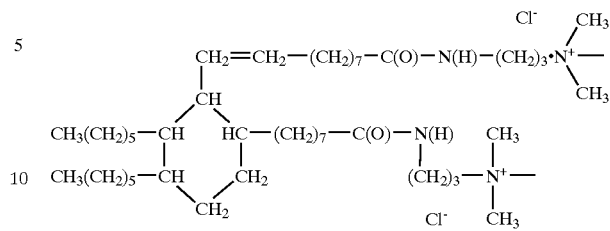

wherein;
x is an integer ranging from 1 to 2000.

10. A quaternary compound of claim 9 wherein R is —$CH_3(CH_2)_6$—.
11. A quaternary compound of claim 9 wherein R is —$CH_3(CH_2)_8$—.
12. A quaternary compound of claim 9 wherein R is —$CH_3(CH_2)_{10}$—.
13. A quaternary compound of claim 9 wherein R is —$CH_3(CH_2)_{12}$—.
14. A quaternary compound of claim 9 wherein R is —$CH_3(CH_2)_{14}$—.
15. A quaternary compound of claim 9 wherein R is —$CH_3(CH_2)_{16}$—.
16. A quaternary compound of claim 9 wherein R is —$CH_3(CH_2)_{18}$—.
17. A quaternary compound of claim 9 wherein R is —$CH_3(CH_2)_{20}$—.
18. A quaternary compound of claim 9 wherein R is —$CH_3(CH_2)_{22}$—.
19. A quaternary compound of claim 9 wherein R is —$CH_3(CH_2)_{24}$—.
20. A quaternary compound of claim 9 wherein R is —$CH_3(CH_2)_{26}$—.

* * * * *